United States Patent [19]

Matschiner

[11] Patent Number: 5,716,795
[45] Date of Patent: Feb. 10, 1998

[54] THROMBOMODULIN-BASED COAGULOMETRIC ASSAY OF THE PROTEIN C SYSTEM

[76] Inventor: John T. Matschiner, 3554 Davenport St., Omaha, Nebr. 68131-2430

[21] Appl. No.: 582,384

[22] Filed: Jan. 3, 1996

Related U.S. Application Data

[63] Continuation-in-part of Ser. No. 481,185, Jun. 7, 1995, Pat. No. 5,525,478, which is a continuation of Ser. No. 771,644, Oct. 4, 1991, abandoned.

[51] Int. Cl.$^6$ .............................. C12Q 1/56; C12Q 1/00; G01N 33/53
[52] U.S. Cl. .............................. 435/13; 435/4; 435/69.6; 435/7.2; 435/7.25; 436/63; 436/69; 514/822; 514/834
[58] Field of Search .............................. 435/13, 4, 69.6, 435/7.2, 7.25; 436/63, 69; 514/822, 834

[56] References Cited

U.S. PATENT DOCUMENTS

| | | | |
|---|---|---|---|
| 4,736,018 | 4/1988 | Revtelingsperger | 514/2 |
| 4,748,156 | 5/1988 | Aoki et al. | 514/8 |
| 4,849,403 | 7/1989 | Stocker et al. | 435/24 |
| 5,001,069 | 3/1991 | Bartl et al. | 436/86 |
| 5,043,425 | 8/1991 | Aoki et al. | 435/70.4 |
| 5,051,357 | 9/1991 | Hassouna | 436/69 |
| 5,055,412 | 10/1991 | Proksch | 435/13 |
| 5,120,537 | 6/1992 | Esmon et al. | 514/21 |
| 5,147,638 | 9/1992 | Esmon et al. | 514/12 |
| 5,279,956 | 1/1994 | Griffin et al. | 514/12 |
| 5,330,907 | 7/1994 | Philapitsch et al. | 435/23 |
| 5,426,097 | 6/1995 | Stern | 514/21 |
| 5,439,802 | 8/1995 | Rosen | 435/13 |
| 5,443,960 | 8/1995 | Dahlback | 435/13 |
| 5,453,373 | 9/1995 | Gerlitz et al. | 514/2 |

OTHER PUBLICATIONS

Faioni et al, "Blood"; vol. 71(4), pp. 940–946, (Apr. 1988).

*Thrombosis and Hemorrhage*, Edited by Joseph Loscalzo, M.D., PhD, et al., "Laboratory Methods in Hemostasis", by P.L. Bockenstedt, Blackwell Scientific Publications, 1994, pp. 455–513.

*Disorders of Hemostasis*, Edited by Oscar D. Ratnoff, M.D., et al., "Hemostatic Disorders Associated With Neoplasia", by George H. Goldsmith, Jr., W.B. Saunders Company, 1991, pp. 352–368.

"Antithrombotic Effect of Recombinant Human Thrombomodulin on Thrombin–Induced Thromboembolism in Mice", by Komakazu Gomi, et al., *Blood*, vol. 75, No. 7 (Apr. 1), 1990, pp. 1396–1399.

"Determination of Protein C in Plasma", by H. Löbermann, et al., Behring Inst. Mitt., No. 79, (1986), pp. 112–120.

"Measurement of Protein C and Protein S in Plasma Samples", by Silvana Viganó–D'Angelo, et al., *Biotechnology in Clinical Medicine*, Edited by A. Albertini, et al., 1987 Raven Press, Ltd., New York, pp. 163–173.

"Biological relevance of the protein C system and laboratory diagnosis of protein C and protein S deficiencies", by Klaus T. Preissner, *Clinical Science*, vol. 78, 1990, pp. 351–364.

(List continued on next page.)

*Primary Examiner*—Louise Leary
*Attorney, Agent, or Firm*—Polster, Lieder, Woodruff & Lucchesi, L.C.

[57] ABSTRACT

The present invention provides a one-stage assay which uses soluble thrombomodulin for directly determining the functional status in plasma of the protein C system. The activity of the protein C system is used to determine the risk of thrombosis in the host individual. Alternatively, the activity of the protein C system is used to determine the presence of a malignant cancer and other pathologies. In another embodiment of the invention, a heparin adsorbent step is added to the assay process which reveals the existence of an additional component in protein C activation, and thus the existence of an additional component in the regulation of blood coagulation.

13 Claims, 4 Drawing Sheets

OTHER PUBLICATIONS

"DADE®/ACTIN® Activated Cephaloplastin Reagent", Liquid Rabbit Brain Cephalin with Plasma Activator, Baxter Healthcare Corporation package insert LI0293-BH-H, Revised Oct. 1988.

"Identification of an endothelial cell cofactor for thrombin-catalyzed activation of protein C", by Charles T. Esmon et al., *Proc. Natl. Acad. Sci. USA*, vol. 78, No. 4, Apr. 1981, pp. 2249–2252.

"Isolation of a Membrane-bound Cofactor for Thrombin-catalyzed Activation of Protein C" by Naomi L. Esmon, et al., *The Journal of Biological Chemistry*, vol. 257, No. 2, Issue of Jan. 25, 1982, pp. 859–864.

*Hematology, Basic Principles and Practice*, R. Hoffmann et al., Churchill Livingstone Inc., 1991.

*Hematology, Basic Principles and Practice*, R. Hoffmann et al., Churchill Livingstone Inc., 1995, Second Edition.

"The Regulation of Natural Anticoagulant Pathways", Charles T. Esmon, *Science*, vol. 235, pp. 1348–1352.

"The Roles of Protein C and Thrombomodulin in the Regulation of Blood Coagulation", Charles T. Esmon, *The Journal of Biological Chemistry*, vol. 264, No. 9, Issue of Mar. 25, 1989, pp. 4743–4746.

"Factor V Leiden—An Unselfish Gene?", Katherine A. Hajjar, M.D., *The New England Journal of Medicine*, vol. 331, No. 23, Dec. 8, 1994, pp. 1585–1587.

"Medical Research Hot Papers", David W. Sharp, *The Scientist*, vol. 9, No. 22, Nov. 13, 1995, p. 15.

"Mutation in the Gene Coding for Coagulation Factor V and the Risk of Myocardial Infarction, Stroke, and Venous Thrombosis in Apparently Healthy Men", Paul M. Ridker, M.D., et al., *The New England Journal of Medicine*, vol. 332, No. 14, Apr. 6, 1995, pp. 912–917.

*Disorders of Hemostasis*, Edited by Oscar D. Ratnoff, M.D., et al., "Normal Hemostatic Mechanisms", by Hidehiko Saito, W.B. Saunders Company, 1991, pp. 18–47.

FIG. 5

TABLE
CLOT TIME (SECONDS) OF THIRTY (30) COMMERCIAL INDIVIDUAL NORMAL CONTROLS
(GEORGE KING BIO-MEDICAL CORE SET OF 30 DONORS)

| SAMPLE # | OBSERVED APTT ± THROMBOMODULIN (TM) | | | | |
|---|---|---|---|---|---|
| | 0 TM | 4 μl TM | 5 μl TM | 6 μl TM* | |
| 1 | 33.3,28.8:31.1 | | | 160.4,169.9:165.2 | |
| 2 | 36.4,35.8:36.1 | 207.6,179.8:193.7 | >250 | >250 | |
| 3 | 36.9,36.7:36.8 | >250 | >250 | >250 | |
| 4 | 28.2,28.8:28.5 | | 209.0,185.4:197.2 | >250 | |
| 5 | 29.6,28.4:29.1 | | 164.0,146.8:155.4 | >250 | |
| 6 | 35.8,35.3:35.6 | 230.3,201.4:215.9 | >250 | >250 | |
| 7 | 43.3,34.8:34.6 | | | 212.4,186.8:199.6 | |
| 8 | 33.4,35.4:34.4 | | | 157.3,162.8:160.1 | |
| 9 | 34.8,32.3:33.6 | | | 141.3,136.3:138.8 | |
| 10 | 26.4,26.4:26.4 | | | 118.2,112.9:115.6 | |
| 11 | 30.7,29.6:30.0 | 145.8,123.3:134.6 | | >250 | |
| 12 | 31.1,28.8:30.6 | | | 222.9,245.4:234.2 | |
| 13 | 32.1,32.9:32.5 | | | 163.3,178.8:171.1 | |
| 14 | 30.8,30.9:30.9 | | 158.9,146.4:152.7 | >250 | |
| 15 | 26.6,25.4:26.1 | | | 168.3,165.8:167.1 | |
| 16 | 27.3,28.4:27.9 | | | 114.9,122.3:118.6 | |
| 17 | 29.4,26.8:28.1 | | | 227.3,>250:227.3 | |
| 18 | 31.8,31.3:31.6 | | | 198.8,183.4:191.1 | |
| 19 | 37.3,36.8:37.1 | | 189.8,194.8:192.3 | >250 | |
| 20 | 33.8,32.8:33.3 | | | 138.4,144.8:141.6 | |
| 21 | 28.7,29.1:28.7 | 143.8,185.9:164.9 | >250 | >250 | |
| 22 | 27.9,26.3:27.1 | | | 92.3,90.8:91.6 | |
| 23 | 26.8,28.4:27.7 | | | 132.2,138.8:135.6 | |
| 24 | 33.8,34.4:34.1 | | 231.3,195.3:312.2 | >250 | |
| 25 | 34.4,28.8:31.6 | | | 248.4,>250:248.4 | |
| 26 | 28.9,25.9:27.4 | 156.1,163.8:160.0 | >250 | 122.3,126.9:124.6 | |
| 27 | 29.4,26.8:28.1 | | | | |
| 28 | 26.1,31.4:28.9 | | >250 | >250 | |
| 29 | 34.9,35.8:35.4 | 106.4,139.9:123.2 | >250 | 171.3,179.1:176.2 | |
| 30 | 32.4,32.1:32.3 | >250 | >250 | >250 | |

* THE AMOUNT OF THROMBOMODULIN OTHERWISE USED ROUTINELY IN THE CLINICAL PHASE OF THIS STUDY. AT 6μl OF ADDED THROMBOMODULIN THE FINAL CONCENTRATION IN THE ASSAY WAS ABOUT 50 nM

TABLE
CLOT TIME (SECONDS) OF THREE SPECIMENS OF POOLED CONTROL
PLASMA TREATED WITH HEPARIN ADSORBENT (SIGMA)

OBSERVED PTT + THROMBOMODULIN (TM)

| PLASMA | 0 TM | 6 µl TM |
|---|---|---|
| FROZEN CONTROL [1] | 32.4, 31.9  32.2 | 89.4, 77.9  83.7 |
| FACTOR REFERENCE [2] | 29.4, 28.4  28.9 | 78.8, 86.4  82.6 |
| CI-TROL (I) [2] | 29.9, 29.3  29.6 | 93.2, 81.8  87.5 |

(UNTREATED PLASMA)

| | | |
|---|---|---|
| FROZEN CONTROL [1] | 31.5 | 187.4 |
| FACTOR REFERENCE [2] | 29.3 | >250 |
| CI-TROL [2] | 32.0 | >250 |

[1] GEORGE KING BIO-MEDICAL

[2] BAXTER-DADE

FIG. 6

THROMBOMODULIN-BASED COAGULOMETRIC ASSAY OF THE PROTEIN C SYSTEM

This application is a continuation-in-part of application Ser. No. 08/481,185 filed Jun. 7, 1995 now U.S. Pat. No. 5,525,478, which is a continuation of application Ser. No. 07/771,644 filed Oct. 4, 1991, now abandoned.

FIELD OF THE INVENTION

The present invention relates to a thrombomodulin-based coagulometric assay of the protein C system which incorporates soluble thrombomodulin and for the rapid and direct in vitro determination of the functional status of the protein C system.

BACKGROUND OF THE INVENTION

The capacity of blood to clot and stop flowing from a wound is dependent on the proper functional interaction of a large number of factors and cofactors in the blood coagulation cascade. The ability of clinical laboratories to reliably and conveniently assay for these factors and cofactors in plasma samples from donor patients can be critical in monitoring individuals for whom either inappropriate coagulation episodes (such as occurs, for example, in disseminated intravascular coagulation disease) or inappropriate failure of blood to clot (such as occurs, for example, in hemophilia) is a daily life-threatening problem.

The physiologic basis for these clinically important coagulation problems can be exceedingly complex to diagnose. In most cases, however, diagnosis can be made by detecting either quantitative or functional changes in certain of the biological factors and cofactors which activate or regulate the coagulation process. A number of diagnostic assays have been developed which reliably measure many of the regulatory proteins involved in the coagulation cascade (see, for example, the textbooks by R. Hoffman et al., *Hematology: Basic Principles and Practice*, New York: Churchill Livingston, Inc., 1991; and by C. Kjeldsberg et al., *Practical Diagnosis of Hematologic Disorders*, Chicago: American Society of Clinical Pathologists Press, 1989). These include such routine coagulation assays as the activated partial thromboplastin time (APTT) assay, the prothrombin time (PT) assay, and the thrombin clotting time (TCT) assay. In spite of extensive research, none of these assays directly measure, in a one-stage assay, the functional status in plasma of the vitamin K-dependent coagulation-inhibiting proteins, protein C and protein S. Because protein C and protein S are both essential in the normal regulatory process of down-regulating the blood coagulation cascade, the lack of any one-stage assay which directly determines both of their functional activities remains a serious deficiency in the art. In addition, there is no known assay which directly measures the functional status of the protein C system. Moreover, when the protein C system is measured in the present invention, high risk for recurrent thrombosis may be identified. The protein C system, as understood by the prior art, is disclosed by C. T. Esmon, *Science* 235, 1348–1352, Mar. 13, 1987, and in *The Journal of Biological Chemistry*, Vol. 264, No. 9, pp. 4743–4746, Mar. 25, 1989, which is hereby incorporated by reference in its entirety. More specifically, Esmon teaches a mechanism for formation and function of activated protein C and interactions within the protein C anticoagulant pathway.

It is noted that there has been some work with protein C in the recent prior art. Hajjar in 1994 wrote that "hereditary resistance to protein C was first described in 1993 in a middle-aged man with familial thrombophilia and a poor in vitro anticoagulant response to activated protein C. In one of the major discoveries about coagulation in the past decade, this disorder was shown to reflect a mutation in coagulation factor V that rendered it resistant to inactivation by protein C." Most notably, less than two months ago, Sharp, *The Scientist* (Nov. 13, 1995), commented on medical research hot papers, specifically commenting on two hot papers showing how a substantial proportion of not otherwise explained venous thrombosis is caused by resistance to activated protein C, the proportion of which depends upon the selection criteria for the study. Sharp acknowledged that in February, 1994, it was suggested that resistance to activated protein C was caused by a single gene and that the defect involved a defective factor V. Subsequently, the defective factor V has been identified as due to a G-to-A point mutation resulting in a protein known as factor V Leiden. Sharp noted that besides being present in over half of people with (familial) thrombophilia, factor V Leiden is unexpectedly common (about 5 percent) in the general population.

Ridker et al., 1995, have recently provided convincing specifications to the thrombotic risk of individuals who carry the factor V Leiden gene. They examined the records of 14,916 predominantly white U.S. male physicians 40 to 84 years old who were free of prior myocardial infarction, stroke, transient ischemic attack and cancer and who had participated in the Physicians' Health Study, a trial of aspirin and beta carotene for the prevention of cardiovascular disease and cancer (final report, 1989). They found that "the prevalence of heterozygosity for the mutation in factor V among men who had myocardial infarctions (6.1 percent) or stroke (4.3 percent) during the study was similar to that among men who remained free of vascular disease (6.0 percent). However, the prevalence of the mutation was significantly higher among men who had venous thrombosis, pulmonary embolism, or both (11.6 percent)." They further reported that the "increased risk was seen with primary venous thrombosis but not with secondary (acquired) venous thrombosis, and it was most apparent among older men."

Saito, stated in 1991 that "the diagnosis of hypercoagulability is essential for the identification of individuals at higher risk for thrombosis and for the early treatment of thrombotic disorders. Routine screening tests, such as the prothrombin time and the APTT, are useful for detection of hypocoagulable states or a bleeding tendency, but not for detection of hypercoagulability. Numerous approaches have been made to devise tests that would identify those patients with hypercoagulability or a thrombotic tendency. Specific, sensitive assays for peptides that are released upon activation of the blood coagulation cascade have been developed. These assays measure FPA, FPB, prothrombin fragment $F_{1+2}$, or the protein C activation peptide in the circulating blood. Assays for activated clotting factor-inhibitor complexes that are formed during blood coagulation have also been described. They include assays for the thrombin-antithrombin III complex and factor $X_a$-antithrombin III complex. It is hoped that the application of these assays will further increase our understanding of the pathophysiology of hypercoagulability." More recently, Bockenstedt in 1994 summarized the matter in the following way: "The complete array of factors that play a role in controlling the evolution of thrombosis remains elusive, however, as evidenced by the inability to identify an abnormal factor in the majority of patients with recurrent arterial and venous thrombosis."

With regard to the diagnostic potential of thrombosis in malignancy, Goldsmith in 1991 stated that "repeated observation of thrombosis preceding the clinical recognition of malignancy has persuaded some authors to recommend that unexplained thrombophlebitis, particularly at an unusual site, should stimulate continued scrutiny for at least two years after the thrombotic event. However, other investigators have found the risk for underlying malignancy in this group to rest principally with cancer readily apparent at the time of the thrombosis. At present, it seems most reasonable to consider strongly the possibility of a coincident occult malignancy in patients with unexplained thrombosis at an unusual site (e.g., upper extremity or hepatic vein) or in patients with recurrent migratory thrombophlebitis, particularly at an age of less than 40."

The coagulation enzyme system. To better appreciate the importance of such assays, and how activated protein C and protein S are involved in regulating the blood coagulation cascade, the following brief description of the coagulation enzyme system is provided.

The blood clotting system may best be viewed as a chain reaction involving the sequential activation of inactive enzyme precursors (zymogens) into active serine proteases. These activation events, which take place on the surfaces of cells such as platelets, white blood cells, and endothelial cells, have been divided into two distinct pathways termed the extrinsic and the intrinsic pathways of coagulation. A clot is generated in the intrinsic pathway by activation of those coagulation components which are all contained in (or are "intrinsic to") whole blood. In the extrinsic pathway, components intrinsic to whole blood are required along with an externally-supplied coagulation-activating substance known as "tissue factor" (also sometimes referred to as thromboplastin, thrombokinase, or blood coagulation factor III). Tissue factor is a cell surface protein extrinsic to blood, and is expressed by cellular injury. Whether a particular coagulation factor becomes activated in the extrinsic or the intrinsic pathway is important in selecting a particular coagulometric assay with which to detect and evaluate that particular factor.

Thrombin. The multistep coagulation chain reaction ultimately produces the enzyme thrombin, the last serine protease in the coagulation cascade, which, through limited proteolysis, converts fibrinogen molecules into an insoluble gel of fibrin fibers which forms the physical clot. Two key events in the coagulation cascade are the conversion of clotting factor X into an activated form, factor Xa, and the subsequent conversion of prothrombin by factor Xa into thrombin. Both of these conversion reactions occur on cell surfaces such as, for example, the surfaces of platelets, and both reactions require cofactors. These cofactors, factors V and VIII, are in circulation in the form of relatively inactive precursor molecules. When the first few molecules of thrombin are formed, thrombin loops back and activates factors V and VIII through limited proteolysis. The activated factors, Va and VIIIa, accelerate both the conversion of prothrombin into thrombin and also the conversion of factor X to factor Xa, speeding the clotting process by approximately 100,000 fold. This significant amplification is essential in the timely formation of a clot. As will be discussed below, factors Va and VIIIa are the principal protein targets of activated protein C and protein S.

The reactions in which thrombin participates occur at different rates and are driven by different concentrations of thrombin. The reaction driven by the lowest concentration of thrombin is the activation of protein C. Another reaction driven by low concentrations of thrombin is the activation of factor VIII. Conversely, a reaction requiring a relatively high concentration of thrombin is the formation fibrin. Accordingly, regulatory reactions are favored over the formation of fibrin.

Thrombomodulin. Some of the thrombin formed during the formation of a clot is also bound by thrombomodulin, an essential reagent used in soluble form in the present invention. Thrombomodulin is a glycoprotein normally found fixed in the surface membranes of endothelial cells that form the lining of all blood vessels. Accordingly, when blood is withdrawn from a blood vessel for analysis, thrombomodulin is left behind. As a consequence, it has not been possible until the present invention to analyze the effectiveness of the protein C system. Instead, what has been done is to measure the activity of specific components of this system, most often protein C. To accomplish this, protein C is either first removed from blood plasma prior to its analysis, or protein C is activated in plasma and then the activated product is removed from plasma for analysis. This is necessary because activation of protein C by physiological agents requires, at a minimum, the addition of thrombin and calcium ions which simultaneously produce fibrin and renders any subsequent coagulometric analysis of the same sample of plasma impossible. While vascular endothelium once was thought to be a passive barrier which simply channeled the blood, it now is known that endothelial cells are actively involved in the regulation of intravascular coagulation mechanisms, and that much of this activity is due to the thrombomodulin in the endothelial cell membranes.

Since the discovery of thrombomodulin, it initially appeared that the protein C system ought to be a broad player in regulation of blood coagulation. However, evidence of its failure to function in most instances of thrombotic disease, arterial and venous, was nowhere to be found. Even so, the importance of protein C was nevertheless confirmed when, in the early 1980's, it was discovered that homozygous protein C deficiency was incompatible with life in the neonatal period. Consequently, those skilled in the art have concluded that most instances of thrombotic disease are caused by some stimulus of procoagulant reactions, and, importantly, not by some failure of anticoagulant reactions, even though the mechanisms of pathological stimulus of procoagulant reactions have not been defined, only speculated.

Thrombin-thrombomodulin complex. Thrombomodulin forms a tight, stoichiometric complex with thrombin, altering both the physical shape and functional properties of thrombin so that it no longer has procoagulant activity, i.e., it no longer converts fibrinogen to fibrin, activates platelets, or converts clotting factors V and VIII to their activated counterparts Va and VIIIa. Rather, the thrombin which is bound by thrombomodulin becomes an efficient activator of protein C. The rate constant for the activation of protein C by thrombin bound in a thrombomodulin-thrombin complex is about 20,000 fold higher than the rate constant for activation of protein C by thrombin found free in solution. Additionally, activation of protein C by thrombin in the absence of thrombomodulin is inhibited by calcium ions, whereas activation by the thrombin/thrombomodulin complex is a calcium-dependent reaction.

Thus, the coagulation-inhibiting effects of thrombomodulin are of two different types. One is a heparin-like anticoagulant effect, in which the binding of thrombin to thrombomodulin inhibits the capacity of thrombin to enzymatically convert fibrinogen into fibrin fibers; the anticoagulant heparin exerts a similar antithrombin effect. This is the thrombomodulin-mediated anticoagulant effect most commonly observed by others (for example, see Gomi et al., *Blood* 75: 1396, 1990).

The second anticoagulant effect of thrombomodulin results from the activation of protein C by the thrombin-thrombomodulin complex. This effect is the key component of the present invention. When activated, protein C has the capacity to enzymatically cleave (via hydrolysis) both factor Va and factor VIIIa, substantially inhibiting both of their clot-promoting activities. In the presence of its vitamin K-dependent cofactor protein S, the rate of activated protein C-mediated hydrolysis of factors Va and VIIIa is increased by about 25 fold compared to hydrolysis in the absence of protein S. Thus, one of the important mechanisms operating in the vascular endothelium to maintain the normal anticoagulant state of the endothelial surface is the pathway by which a thrombin-thrombomodulin complex activates protein C to form a coagulation-inhibiting activated protein C-protein S complex on a cell surface.

The vitamin K-dependency of the protein C and protein S coagulation-inhibiting proteins derives from the fact that a vitamin K-dependent microsomal carboxylase enzyme in the liver forms an unusual amino acid, gammacarboxyglutamic acid, in a post-ribosomal carboxylation step in the precursor proteins of both protein C and protein S. The appearance of the gammacarboxyglutamic acid moieties in these protein molecules is crucial in that it facilitates their efficient binding, via a calcium-mediated bridge, to phospholipid-containing surfaces such as, for example, the surfaces of platelets, endothelial cells, and importantly for in vitro coagulometric assays, phospholipid micelles in solution. As noted below, the binding of the carboxylated glycoproteins to a phospholipid surface allows the proteins to concentrate, interface, and interact with one another more efficiently in three-dimensional space. Several in vitro clotting assays take advantage of this fact, in that phospholipids are included among the necessary reagents used in the coagulometric assays.

Phospholipid. All clotting reactions with meaningful rates are viewed as occurring on a surface. Crucial to the efficient interaction of thrombomodulin (the cofactor), thrombin (the enzyme), and protein C (the substrate) is the presence of calcium ions and an integrating surface such as is found, for example, on a soluble phospholipid micelle (a submicroscopic phospholipid sphere). On such a surface, the three reactants are brought into close proximity, thereby substantially increasing their effective concentrations and their reaction rate many fold. It is believed that all relevant soluble complexes which contain soluble thrombomodulin, thrombin and activated protein C, and which produce vitamin K-dependent anticoagulant activity, also contain an essential surface component. The in vitro clotting assays of the present invention take advantage of this fact by the use of a suitable phospholipid (cephalin) in a preferred embodiment.

Protein C and Protein S assays. Until the present invention, it has not been possible to conveniently measure the functional activities of both protein C and protein S in a simple and rapid one-stage in vitro assay. In addition, it has not been possible to conveniently measure the functional activity of the protein C system. This is because soluble thrombomodulin has never before been added directly into laboratory coagulometric assays to detect protein C zymogen. Rather, thrombomodulin has been added with thrombin as a preactivation reagent, either as a soluble complex, or in an immobilized form and in conjunction with a process which required either prior separation of protein C from other plasma components or the subsequent removal of activated protein C from other plasma components in order to carry out the final determination of activated protein C in a separate coagulometric or amidolytic assay. Thus, the anticoagulatory effect of soluble thrombomodutin, in the form of soluble thrombomodulin-thrombin complexes, has never been exploited directly in conventional clinical assays.

Protein C Assays. For protein C, a number of different assays are available for its determination (as reviewed in detail by Loberman et al., *Behring Inst. Mitt.* 79:112, 1986; Vigano-D'Angelo et al., in *Biotechnology in Clinical Medicine* [Albertini et al., editors] New York: Raven Press, 1989; and more recently by Preissner, *Clin. Sci.* 78:351, 1990). The assays generally fall into three categories: antigenic detection assays, chromogenic (amidolytic) assays, and functional coagulometric assays.

Assays for the activity of protein C were cumbersome, complicated, and in several cases, required reagents not readily commercially available, and which were not precise until a snake venom that activated protein C was discovered by Stocker. See U.S. Pat. No. 4,849,403 to Stocker which is hereby incorporated by reference in its entirety.

Protein C antigenic assays. For determination of protein C antigen concentration in plasma, detection assays include electroimmunoassay, radioimmunoassay, and ELISA-type assays. Not only polyclonal antibodies from rabbit or goat, but also monoclonal antibodies have been used as detecting reagents in these assays. While in vitro detection of protein C with antibodies is a sensitive procedure, antigenic detection provides little or no information regarding the functional capacity of the protein C detected.

Protein C chromogenic assays. Alternatively, because activated protein C is an enzyme, its presence in a plasma sample can be quantified with a chromogenic substrate. Prior activation of protein C, with exposure of the enzymatic active site, is required for expression of its enzymatic activity. However, the relatively small size of the synthetic chromogenic substrate (about 600 daltons) commonly used in these assays may permit satisfactory proteolysis of the synthetic substrate, while missing defects in the functional integrity of protein C which would prevent proteolytic cleavage of factor Va and VIIIa, the biological substrates of activated protein C which each have molecular weights of about 300,000 daltons. Moreover, the interaction of activated protein C with its cofactors (protein S, calcium ions, and phospholipid), which requires that all functional features of the protein C molecule be intact, is not evaluated by chromogenic assays. It is important to be aware of this, since protein C molecules detected in chromogenic assays can still be deficient in functional anticoagulant capacity.

Protein C coagulometric assays. For determination of functional capacity of protein C molecules in a plasma sample, coagulometric assays offer the advantage of evaluating the coagulation-inhibiting activity of activated protein C in the presence of its usual biological substrates and cofactors, thereby reflecting more accurately the physiologic state of the protein C in the particular plasma sample being evaluated.

The protein C in a plasma sample is commonly activated before it is assayed. This activation is done either with or without prior separation of protein C from other plasma components. Isolation of the protein C from the test plasma sample has (up until the present invention) been necessary if the protein C is to be activated by thrombin or by the physiological activator, which is the thrombin/thrombomodulin complex. Unfortunately, because of poor reaction kinetics, activation of protein C with thrombin in the absence of thrombomodulin does not lead to complete activation of protein C in the sample. In contrast, when thrombin is bound to thrombomodulin, the rate of activation is increased by about 20,000 fold over the rate obtained with thrombin alone.

After either of the above procedures, the anticoagulant activity of activated protein C is assessed most commonly either by prolongation of the otherwise routine activated partial thromboplastin time (APTT) assay, or in a factor Xa one-stage coagulometric assay. The clot time in this latter assay is a function of the conversion of prothrombin to thrombin, and is initiated by the addition of exogenous factor Xa to the plasma sample in the presence of calcium ions and a phospholipid component. The assay is sensitive to activated factor V, but not to activated factor VIII. In this system, addition of preactivated protein C from the test plasma sample to a control plasma sample prior to the addition of factor Xa prolongs the clot time as a result of its ability to inactivate factor Va generated during the reaction.

In stark contrast to the commonly used assays discussed above, the assay of the present invention does not require preliminary isolation of protein C from a plasma test sample; it permits the activation of protein C with its physiological activator, the thrombin/thrombomodulin complex; and it results in a determination of protein C functional activity in the test sample, all in a simple one-stage procedure.

Protein S assays. Laboratory evaluation of protein S status is complicated by the fact that two forms of protein S are present in plasma. In plasma, about 40% to 50% of the protein S is free and serves as the cofactor for activated protein C. The remaining 50% to 60% of plasma protein S is complexed to C4b binding protein ("C4bBP") and, as such, is unavailable as an anticoagulant. That C4bBP is an acute phase protein and is elevated during inflammation, further complicates evaluation of protein S status. This rise in C4bBP favors a transient shift of the protein S to the complexed form, thereby inducing a relative and transient protein S deficiency state. Because protein S which is bound to C4bBP in plasma is no longer able to function as a cofactor with activated protein C, individuals with serious inflammatory disorders are often at risk for thrombosis. This is an acquired situation which will rise and fall, and even disappear, depending on the state of the inflammatory disorder.

In the clinical laboratory, a very limited number of tests are available to assess protein S status, and these are generally antigen detection assays. These tests include polyethylene glycol precipitation of bound protein S with subsequent measurement of the free protein S remaining in the plasma; crossed immunoelectrophoresis for protein S, which separates free and bound forms of protein S, but is not quantitative; and enzyme-linked immunosorbent assays (ELISA). ELISA assays are suitable in combination with PEG precipitation to quantitate free protein S. However, while ELISA assays may detect protein S with sensitivity, such antigen detecting assays provide little or no information regarding the functional capacity of the protein S detected.

The diagnosis of cancer is, in certain instances, closely related to thrombotic risk. Specifically, many forms of cancer are accompanied by the risk of thrombosis. Significantly, even in early, undiagnosed stages of cancer an increased risk of thrombosis is observed. See, Goldsmith, 1991, which is hereby incorporated by reference in its entirety. As a result, an assay which shows an increased risk of thrombosis could serve as an early detection which sensitizes the physician to a potential diagnosis of cancer.

Accordingly, there is a need in the art to provide a convenient and reliable one-stage assay by which the activity of the entire protein C system as a whole is determined.

There is also a need in the art to provide a convenient and reliable one-stage assay by which protein C and protein S can be quantitatively and functionally determined in a blood plasma test sample in a clinical laboratory.

There is also a need in the art to provide an assay which functions as a broadly applicable indicator of arterial and venous thrombotic risk, and as an aid in the timely diagnosis of cancer.

There is a further need in the art to provide a method of isolating a previously unrecognized component in the protein C system which is therapeutically useful in oncology and vascular disease as an anticoagulant.

SUMMARY OF THE PRESENT INVENTION

It is in view of the above needs that the present invention answers. While the prior art focuses on primary (hereditary or familial) thrombotic risk and evaluation of specific components of the protein C system, the present invention provides an assay which is directed to primary and secondary (acquired) thrombotic risk by evaluation of the protein C system as a whole.

In accordance with the present invention, there is provided a one-stage blood coagulation assay which uses soluble thrombomodulin for determining the functional status of the protein C system in plasma. The method comprises combining a blood plasma sample and a coagulation-activating substance in a calcium-free solution, then adding soluble thrombomodulin and calcium ions in amounts sufficient to initiate a coagulation reaction, measuring the time required for the plasma test sample to clot, comparing the measured clot time to that of standard control plasma samples, and then using the compared clot time values for determining the risk of thrombosis in the individual from whom the plasma test sample was taken.

In a preferred embodiment of the present invention, soluble thrombomodulin is added immediately prior to the addition of calcium ions (i.e., the recalcification step), and the subsequent extension of the clot time caused by the anticoagulant effect of the soluble thrombomodulin is compared to the extension of clot time that is observed in normal and protein C-deficient plasma samples used as normal and deficient plasma controls, respectively.

The coagulation-activating substance added to the mix of reagents at the beginning of the assay of this invention is, in the preferred embodiment, the "DADE®/ACTIN® ACTIVATED CEPHALOPLASTIN REAGENT." This reagent is available commercially from the Baxter Healthcare Corporation (now Dade International) and is more fully described in its package insert No. L10293-BH-H (revised 10/88) (Baxter/Dade, Miami, Fla.), the content of which is incorporated herein by reference. The coagulation-activating ingredient in this reagent is ellagic acid, a negatively-charged organic compound of formula $C_{14}H_6O_8$, having a molecular weight of about 302 daltons.

In another embodiment, it is expected that coagulation-activating substances include negatively-charged collagen molecules; or negatively-charged foreign surfaces such as micronized silica, kaolin, fine glass or metal beads, and even wooden applicator sticks. The use of these latter particulates are limited, however, to assays in which the presence of such insoluble foreign surfaces will not interfere in carrying out the assay.

In the preferred embodiment of the present invention, the phospholipid added to the assay is cephalin, a glycerophosphoric acid extracted from dehydrated rabbit brain, and contained as an active ingredient in the "DADE®/ACTIN® ACTIVATED CEPHALOPLASTIN REAGENT," as more fully described in the Baxter Healthcare Corporation package insert No. L10293-BH-H [revised 10/88](Baxter/Dade, Miami, Fla.). Biochemically, cephalins consist of glycerophosphoric acid in which the two free hydroxyls of the molecule are esterified with long-chain fatty acid residues, and ethanolamine forms an ester linkage with the phosphate group. All natural cephalin products occur in alpha-forms, which have the following generic structure:

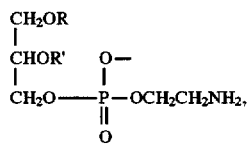

where R and R' can be, but are not necessarily, identical fatty acids.

Other phospholipids which may be used in further embodiments of the present invention are those which successfully facilitate the activation of protein C and its detection in the coagulometric assays of the present invention. It is believed that all relevant soluble complexes which contain soluble thrombomodulin, thrombin, and activated protein C, and which produce vitamin K-dependent anticoagulant activity, also contain an essential surface component. The in vitro clotting assays of the present invention take advantage of this fact by the use of a suitable phospholipid (cephalin) in a preferred embodiment. However, besides phospholipids, any micelle-forming (or liposome-forming) ingredient which is amphipathic and whose charge distribution and size make it optimal for use as a surface carrier in facilitating the coagulometric assays disclosed in the present invention is included within the scope of the coagulation-activating agents of the present invention.

In a variation of the present invention, a method for monitoring the isolation of a previously unrecognized component in the protein C system which is therapeutically useful in oncology and vascular disease as an anticoagulant is provided. The method comprises removing said component from a blood plasma sample, combining the blood plasma sample and a coagulation-activating substance in a calcium-free solution, then adding soluble thrombomodulin and calcium ions in amounts sufficient to initiate a coagulation reaction, measuring the time required for the plasma test sample to clot, comparing the measured clot time to that of protein C-deficient and normal control plasma samples, and then using the compared clot time values for determining the loss of anticoagulant activity of the protein C system.

By the term "normal control plasma" as used above and hereinafter is meant a plasma sample which contains the usual (statistically common) and expected amounts of all known coagulation-related factors which are essential in promoting the clotting of plasma by either the intrinsic or the extrinsic coagulation pathways. Such factors are known to those skilled in the art, and usual (statistically common) values, with normal range of values, are to be found in such well-known textbooks as that by C. Kjeldsberg et al., *Practical Diagnosis of Hematologic Disorders*, Chicago: American Society of Clinical Pathologists Press, 1989. It is also standard practice in the art to combine plasma samples from a large number of normal, healthy volunteer donors to generate a larger "pooled" batch of normal plasma. The advantage of such a pool is that normal plasma samples with identical control values will be available over a long period of time, especially if such standardized control samples are preserved in a frozen or lyophilized (freeze-dried) state.

The terms "test sample" or "plasma test sample" as used above and hereinafter simply refer to a plasma sample in which the content of components of the protein C system are not yet known, and which is the subject of the coagulometric assay.

It is to be understood that any of the preferred assays of the present invention, when properly set up, can be used to detect the presence or the functional activity of components of the coagulation-inhibiting protein C system in a plasma sample, e.g., they can be used to detect or to measure protein C and/or protein S qualitatively or quantitatively, respectively. Thus, the terms "detect" and "detecting," "measure" and "measuring," and "determine" and "determining" as used above and hereinafter are meant to cover both the quantitative and the qualitative aspects of the assays.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 5 is a table which summarizes the clot time in seconds of 30 commercial individual normal blood plasma samples.

FIG. 6 is a table which summarizes the clot time in seconds of 3 specimens of pooled control plasma treated with heparin adsorbent.

DETAILED DESCRIPTION OF THE PRESENT INVENTION

Figure 1:
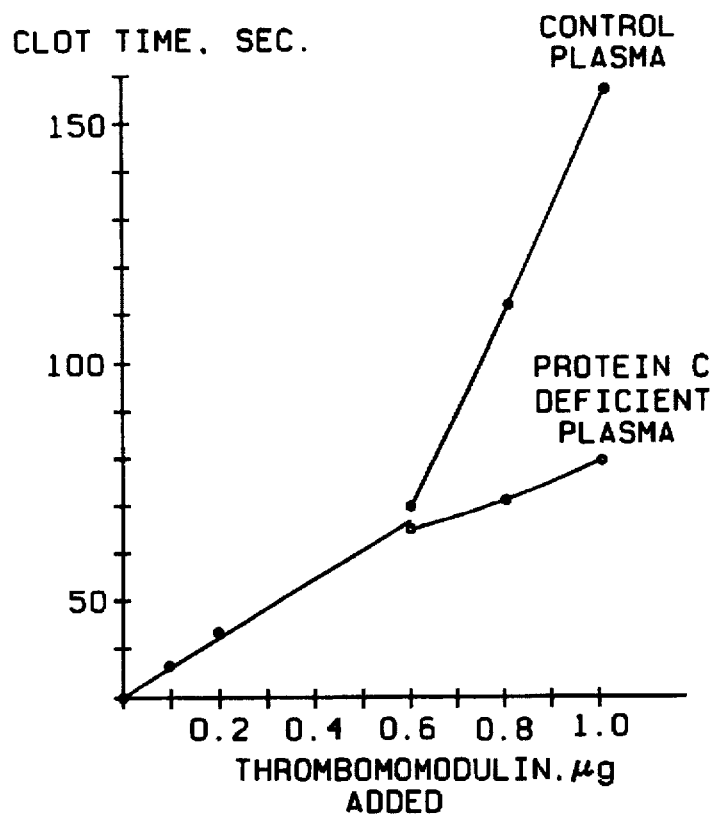
FIG. 1 is a line graph which demonstrates that inclusion of soluble thrombomodulin in a coagulometric assay has a significantly different anticoagulant effect on a protein C-deficient plasma sample than it does on a normal control plasma sample. The final amount of soluble thrombomodulin (in micrograms) added to the assay is plotted versus clot time (in seconds) for each sample mixture. The curve with filled circles (●) represents the normal control plasma, and the open circles (○) represent the protein C-deficient plasma.

One-stage coagulometric assay of the present invention.

The following is a detailed description of the assay of the present invention useful for directly determining in a plasma sample the functional activities of the protein C system. Also provided are descriptions of the necessary reagents and instrumentation used in a preferred embodiment of the present invention. The invention takes advantage of the kinetic environment of an in vitro coagulometric assay to detect the thrombin-mediated coagulation-inhibiting activity of the protein C system, and does so, in a preferred embodiment, in an assay in which all of the clotting factors of the intrinsic (in contradistinction to the extrinsic) coagulation pathway are involved, including clotting factors V and Va, and VIII and VIIIa.

Plasma specimen collection and preparation. In preparing plasma specimens for analysis in the coagulometric assay of the present invention, nine parts of freshly-collected patient blood are mixed thoroughly with one part of 3.8% sodium citrate anticoagulant. The anticoagulated blood specimen is then centrifuged for a minimum of 10 minutes at 1000×G to pellet the large cellular components of the blood. The supernatant plasma is removed to a plastic tube and stoppered until used. Patient plasma is tested within four hours of blood collection at room temperature to ensure validity and reproducibility of results. If the assay cannot be performed within four hours, the plasma is frozen to −70° C. within four hours for preservation until it is thawed for analysis. Human plasma prepared in a similar manner can also be obtained from American Red Cross blood centers.

Coagulation-activating substances. In performing the coagulometric assay of the present invention, the preferred reagent for use in initiating coagulation in the assay cup is the "DADE®/ACTIN® ACTIVATED CEPHALOPLASTIN REAGENT," commercially supplied by Baxter Healthcare Corporation (now Dade International), and described in the Baxter Healthcare Corporation package insert No. L10293-BH-H (revised 10/88). The active ingredients in this commercial reagent are the negatively-charged organic compound, ellagic acid, and the phospholipid, cephalin, extracted from dehydrated rabbit brain.

Other reagents used in the one-stage coagulometric assay. The following reagents are also required for use in the one-stage coagulometric assay of the present invention:

1) saline, prepared as a 0.9% sodium chloride solution in water;
2) soluble thrombomodulin, isolated from rabbit lung tissue and purified according to the procedures of Esmon et al., *The Journal of Biological Chemistry*, Vol. 257, No. 2, pp. 859–864, Jan. 25, 1982, and prepared in a solution of detergent and buffered saline at a final concentration appropriate to the assay; and
3) calcium chloride, prepared as a 25 millimolar solution in water.

The crucial feature of the assay of this invention is the use of soluble thrombomodulin as an additive to the coagulation reaction mixture. The use of soluble thrombomodulin for the activation of protein C in an in vitro coagulometric assay is believed to be unique. When added to the other reagents in the reaction mixture, soluble thrombomodulin provides a highly reactive substrate for the subsequent high-affinity binding of free thrombin. In the presence of calcium, the thrombin in the thrombin-thrombomodulin complex then activates protein C, which, together with protein S, degrades the clot-promoting factors Va and VIIIa in the plasma. Thus, using soluble thrombomodulin as one of the assay reagents, and using protein C- and protein S-deficient plasma samples as deficient plasma controls, the coagulation-inhibiting activities of the protein C system can be directly determined in a one-stage assay procedure.

As noted above, the coagulometric assay of this invention for the protein C system is a one-stage assay because the assay is characterized by a single incubation. In contrast, the prior art assays for protein C activate protein C during a prior preactivation step, followed by an incubation to detect the activated protein C formed, and thus, constitute two-stage assays.

In one embodiment of this invention, the active ingredients and other reagents and controls of this invention constitute the components of a commercial assay kit for determining the functional status of the protein C system. For example, in addition to the soluble thrombomodulin and the coagulation-activating agent of this invention, such a kit optionally contains one or more components selected from (i) a positive control, e.g., a normal plasma sample, (ii) a negative control, e.g., protein C and/or protein S-deficient plasma samples, and (iii) a buffered solution containing a calcium salt, e.g., calcium chloride.

Instrumentation used. In a preferred embodiment of the present invention, a Fibrometer™ coagulation timer (Becton, Dickinson and Company, Rutherford, N.J.) is used to determine the clot time in the coagulometric assay. When the Fibrometer™ is used, the probes must be thoroughly washed with distilled water and wiped dry with lint-free tissue between tests to prevent carryover of activated plasma proteins. Since there are two different types of probes available for this instrument, a 0.3-ml probe and a 0.4-ml probe, it is necessary to design the assay so that the final volume of reagents added to the reaction cups matches the requirements of the probe which is used. It is noted that automated machines commercially available shut off automatically after about 100 seconds and cannot be adjusted to run in the range of clot times needed to run the assay of the present invention, i.e., 90–250 seconds. Accordingly, commercialization of the assay of the present invention will require that the present automated machines be modified accordingly.

Coagulation controls. With each series of tests, standard clot time curves are prepared using several control plasma samples in order to ensure the quality, reproducibility, and interpretability of the data obtained. The control plasma samples are run in the same manner as the test samples, and establish a range of allowable variation for the control clot time values.

In the present invention, protein C-deficient and protein S-deficient plasma samples, used as factor-deficient plasma controls, were prepared by immunoadsorption of different batches of the same citrated human plasma. Immunoadsorption was carried out using immobilized polyclonal antibodies. For example, to prepare protein C-deficient plasma, citrated plasma was mixed in a batch preparation immunoadsorption procedure with anti-protein C coupled to Sepharose®. In contrast, to prepare protein S-deficient plasma, plasma was passed over a polyclonal antibody-Sepharose® affinity column, in a chromatography process well known in the art. Regardless of the immunoadsorption method used, however, it must be noted that the concentration of factors V and VIII may be altered during the processing. Since these factors are crucial in the clotting cascade and are the principal protein targets of activated protein C and protein S as described earlier, alterations in their concentrations will affect the coagulability of and the outcome of assays using the processed plasma samples. Accordingly, the concentrations of factors V and VIII in processed plasma samples must be standardized following immunoadsorption.

Assay Results. The results obtained in the coagulometric assays of the present invention are reported in seconds, and are related to a range of clot time values obtained in each laboratory. This range is established by obtaining plasma samples from a large number of normal healthy donors (for example, from 25 to 40 individuals), and determining the range of statistically common clot time values for these normal donors when tested in the same laboratory. The number of donors needed to establish a statistically acceptable range is determined by each laboratory. Blood is collected by the same method used for collecting test samples from patients, and clot times, using the assay of the present invention, are determined on each normal citrated plasma.

In like manner, a range of values common to populations other than normal, healthy adults is also established as warranted. For example, it may be of interest to establish normal ranges in selected age groups such as pediatric groups or the elderly; or in certain risk groups such as smokers, alcoholics, or individuals on certain medications.

The following examples demonstrate methods and describe protocols useful in practicing the thrombomodulin-containing APTT (hereinafter termed "TM-APTT") assay of the present invention.

EXAMPLE 1

A one-stage functional assay of protein C in normal plasma.

In these studies, a Becton-Dickinson Fibrometer™ with a 0.4-ml probe was used. The following reagents were placed into a coagulation cup, with care to add them quickly, but accurately:

a) 0.1 ml of the "DADE®/ACTIN® ACTIVATED CEPHALOPLASTIN REAGENT" (as described herein above);

b) 0.1 ml of normal plasma or protein C-deficient plasma. As soon as these reagents were added into the cup, a timer was started, the reagents were mixed well, and incubated at 37° C. for exactly 90 seconds. During this brief incubation time, the calcium-independent preactivation of the intrinsic coagulation cascade begins, with the activation of factor XII by kallikrein on negatively charged surfaces, forming factor XIIa, an enzyme which catalyzes the conversion of factor XI, a proenzyme, to its active enzyme form, factor XIa. The rapid preactivation process stops here, in the absence of added calcium ions. At 90 seconds, the following were then added:

c) from 1 to 10 microliters of soluble thrombomodulin (equivalent to 0.1 to 1 micrograms of soluble thrombomodulin, respectively);

d) sufficient volume of prewarmed (37° C.) saline to bring the volume to 0.1 ml;

e) 0.1 ml of prewarmed 25 mM $CaCl_2$.

The total volume in the coagulation cup was 400 microliters. Precisely as the calcium chloride was added, the Fibrometer™ timer and probes started automatically. The elapsed time until detection of a fibrin clot was determined automatically by the instrument. The indicated clot time was recorded for each assay cup in a replicate group.

The amount of soluble thrombomodulin added to the coagulometric assay was important. As shown in TABLE 1, the anticoagulant effect of soluble thrombomodulin in the presence of normal control plasma increased in direct proportion to the amount of thrombomodulin added to the assay. The control assay cup which contained only dialyzing buffer, and which lacked thrombomodulin, clotted in 30.4 seconds, whereas the addition of 1 microgram of soluble thrombomodulin increased this clot time more than five fold.

TABLE 1

Clot time (seconds) in coagulometric assay containing different amounts of soluble thrombomodulin.

| Thrombomodulin | Clot time (seconds) | |
|---|---|---|
| (micrograms) | Control Plasma | Deficient Plasma |
| 0.1 | 37.9 | |
| 0.2 | 43.9 | |
| 0.6 | 69.8 | 64.8 |
| 0.8 | 112.9 | 71.8 |
| 1.0 | 156.9 | 81.3 |
| buffer only | 30.4 | |

*Plasma was deficient in protein C

These data also demonstrate that soluble thrombomodulin had a significantly different anticoagulant effect on protein C-deficient plasma than it did on normal control plasma. When these same data were plotted as amount of soluble thrombomodulin added (in micrograms) versus clot time in seconds), two very different clot time lines were obtained, as shown in FIG. 1.

It is important at this point to realize that the principal difference between the two plasma samples in this test was the presence of functional protein C molecules in the normal plasma sample compared to the absence of these molecules in the protein C-deficient plasma sample. Thus, the difference in slope of the two lines in FIG. 1 reflects primarily the presence or absence of this coagulation-inhibiting protein.

Since soluble thrombomodulin exerts dual anticoagulant functions (one being its heparin-like effect which prevents thrombin from converting fibrinogen into fibrin; and the other being its role in converting protein C into activated protein C, which then degrades factors Va and VIIIa in the coagulation cascade), the clot time curve associated with the protein C-deficient plasma is a reflection solely of the heparin-like activity of thrombomodulin. In contrast, the clot time curve of the normal plasma is a reflection of the combination of the heparin-like activity of thrombomodulin and its protein C activating capacity. Hence, the difference in the clot times between the two curves in FIG. 1 is a novel and simple way to demonstrate and quantify the functional presence of protein C in the normal plasma sample.

EXAMPLE 2

Sensitivity of the one-stage coagulometric assay for determining protein S and protein C functional deficiencies in plasma. A one-stage functional assay of both protein C and protein S was set up essentially the same as in EXAMPLE 1, except that: a) a constant amount (1 microgram) of soluble thrombomodulin was added to each assay cup; and b) the normal and deficient plasma samples were mixed together in varying proportions, in a final volume of 100 microliters, to create a series of plasma test samples with different levels of protein C or protein S, from 100% down to 0% of normal. The normal control plasma had full protein C and protein S activity.

Figure 2:
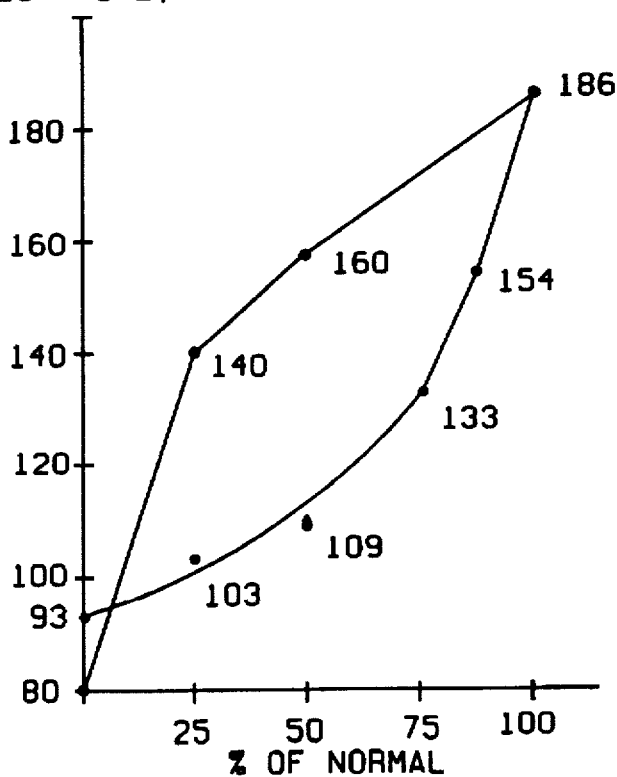
FIG. 2 shows the results of coagulometric assays in which protein S and protein C functional activity are determined using the same methodological embodiment of the present invention. The concentration of normal plasma used to dilute each of the protein C- and protein S-deficient plasma samples is plotted versus clot time (in seconds) for each sample mixture. In this series of studies, an identical amount (about one microgram) of soluble thrombomodulin was added to each assay cup. The filled circles (●) identify the protein C curve, and the open circles (○) identify the protein S curve. The point identified by the open triangle (Δ) marks the clot time of a mixture of 50% S-deficient and 50% C-deficient plasma.

The results from these experiments are shown in FIG. 2, in which the filled circles (●) identify the protein C curve, and the open circles (○) identify the protein S curve. The point identified by the open triangle (Δ) marks the clot time of a mixture of 50% S-deficient and 50% C-deficient plasma.

The clot time curves for the protein C- and protein S-deficient plasma types were substantially different, as shown. Bearing in mind that the part of an assay dilution curve wherein the assay is most sensitive to a change in the concentration of the measured protein is the region comprising the steepest part of the curve, it is clear that the relative dilutions of protein C- or protein S-deficient plasma at which the coagulometric assays are most sensitive for those factors are substantially different. As shown in FIG. 2, the clot time curve using protein C-deficient plasma is steeper (and therefore more sensitive) in the range of 50% or greater normal plasma than it is in the range of 0% to 50% normal plasma. In contrast, the protein S clotting curve is much steeper (and therefore more sensitive) in the range of from 0% to 25% normal plasma.

These data indicate that:

a) assays to detect protein S functional deficiencies can be satisfactorily performed using dilute preparations of the patient plasma test sample (i.e., small volumes of test plasma relative to the volume of protein S-deficient plasma); and that b) under the same reaction conditions (i.e., about 1 microgram of thrombomodulin in the assay), assays for the sensitive detection of protein C functional deficiencies can be performed using small volumes of protein C-deficient plasma mixed into a normal control plasma sample.

These data indicate that, under the same reaction conditions outlined above (i.e., approximately 1 microgram of thrombomodulin in the assay), assays to detect protein C functional deficiencies permit significantly smaller amounts of protein C-deficient plasma to be mixed into the test plasma sample (i.e., cannot be carried out satisfactorily on dilute preparations of the patient plasma test sample if the diluent is protein C-deficient plasma). Under these conditions, protein C in small amounts of test plasma, may be satisfactorily measured by admixture with normal control plasma, thus taking advantage of the sensitive range of protein C detection shown in FIG. 2.

In an effort to improve the sensitivity with which protein S functional deficiencies could be detected, the amount of soluble thrombomodulin in the coagulometric assay of the present invention was raised from about 1 microgram (as used above in EXAMPLE 2) to about 2 micrograms, as shown in the following example.

EXAMPLE 3

Use of higher concentrations of soluble thrombomodulin to determine protein S function.

Figure 3:
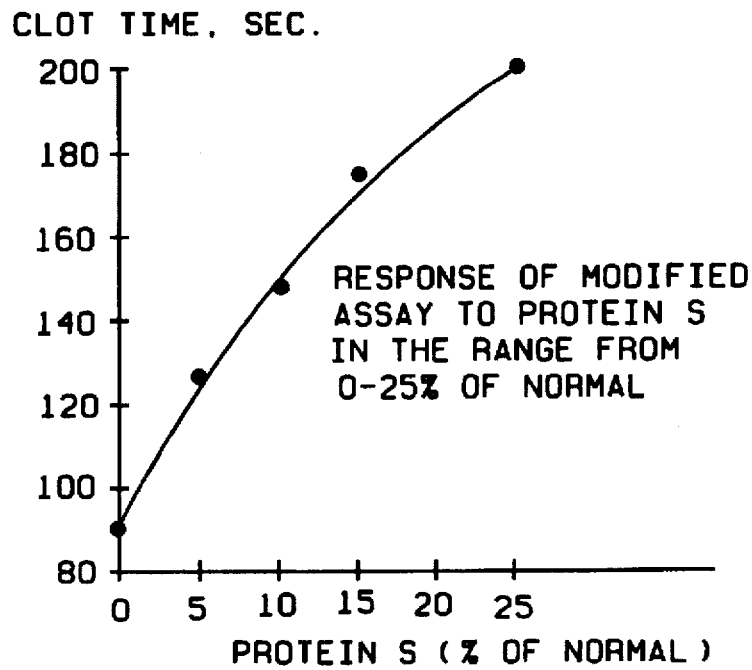
FIG. 3 show he results of a coagulometric assay in which protein S functional activity was determined in a normal plasma sample. The concentration of normal plasma added to a protein S-deficient plasma sample is plotted versus clot time (in seconds) for each sample mixture. In contrast to the data if FIG. 2, the amount of thrombomodulin used in these assays was about 2 micrograms (instead of about 1 microgram) to determine if higher thrombomodulin levels would make the protein S functional assay more sensitive, and therefore more useful, for determining protein S functional activity.

Doubling (to about 2 micrograms) the amount of soluble thrombomodulin reagent added to the coagulometric assay made the assay more sensitive to determining protein S functional activity. The sensitivity with which protein S functional deficiencies in plasma are detected is dependent on the concentration of thrombomodulin used in the assay. As shown in FIG. 3, a substantial range of clot times (from approximately 90 seconds to 200 seconds; a range of about 110 seconds) was observed when protein S was assayed at concentrations varying from 0% (equivalent to 100% protein S-deficient plasma) to 25% of normal (equivalent to 3 parts protein S-deficient plasma to 1 part normal plasma). Thus, by adding about 2 micrograms of soluble thrombomodulin to the assay system, the assay became substantially more sensitive to protein S in the test samples than was detected using only about 1 microgram of soluble thrombomodulin. Therefore, the sensitivity with which protein S functional deficiencies in plasma are detected is dependent on the concentration of thrombomodulin used in the assay.

It was important to compare these results with those of an assay for protein S based on adding exogenous, preactivated protein C into a coagulometric assay. The following example demonstrates that, in the absence of soluble thrombomodulin, the results were substantially different and were not as useful as the results obtained from assays which incorporated soluble thrombomodulin.

EXAMPLE 4

Figure 4:
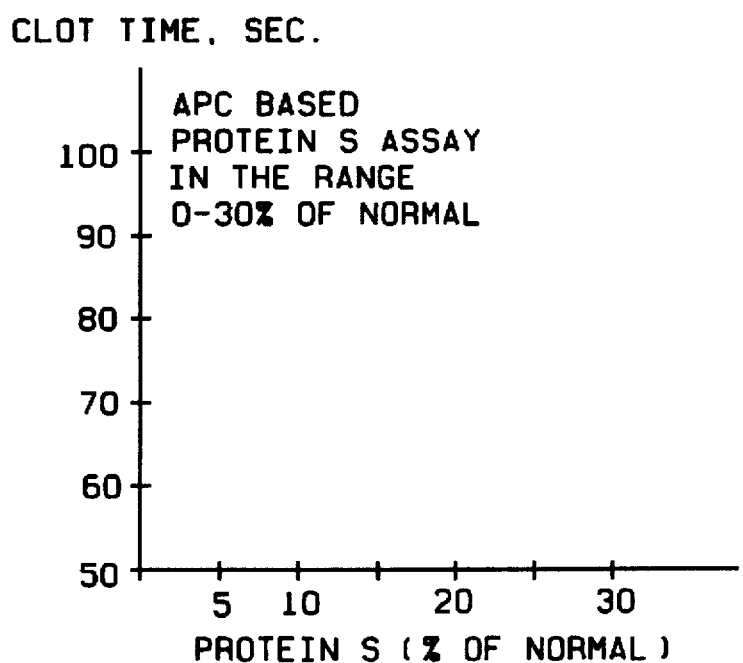
FIG. 4 shows the data from a coagulometric assay in which protein S functional activity was determined in a normal plasma sample to which pure in vitro-activated protein C, but not soluble thrombomodulin, was added at the beginning of the assay. The concentration of normal plasma added to a protein S-deficient plasma sample is plotted versus clot time (in seconds) for each sample mixture.

Adding activated protein C instead of soluble thrombomodulin to a coagulometric assay for protein S. The data in FIG. 4 were obtained in an assay which utilized activated protein C, but not soluble thrombomodulin, as a coagulation-inhibiting protein factor. In a Fibrometer™ coagulation cup, the following were added:

a) 0.1 ml of "DADE®/ACTIN® ACTIVATED CEPHALOPLASTIN REAGENT" described in detail above;

b) 0.1 ml of plasma; and c) 2.0 μl of buffered solution containing 0.4 μg of activated protein C.

These reagents were incubated at 37° C. for exactly 90 seconds, at which time 0.1 ml of saline was added, followed immediately by 0.1 ml of calcium chloride, activating the clotting reaction and the instrument timer.

The data show that the range in clot time (from approximately 54 seconds with undiluted protein S-deficient plasma, to about 89 seconds with 75% protein S-deficient plasma; a range of only about 35 seconds) was approximately one-third of the range in clot time shown in FIG. 3 in the previous example. Because the change in reagents reduced the range of assay responses by nearly 67%, it is clear that adding activated protein C instead of soluble thrombomodulin into the coagulometric assay did not provide as useful a measure of protein S function as was found in the coagulometric assay of the previous examples.

PHASE II CLINICAL STUDY

The original intent of the clinical study was to examine the plasma from a group of healthy donors to get an estimate of the normal range of values for the assay, followed by assays of plasma from a few selected groups of patients who had pathologies or conditions characterized by the risk of thrombosis. However, since deficiencies of protein C and protein S are relatively rare, plasma was collected from hospital and clinical patients who had shown a normal prothrombin time (PT) and a normal activated partial thromboplastin time (APTT), healthy or not. The normal range of protein S concentration (about 25% of the mean) was not expected to appreciably affect clot times of these hospital and clinic samples. The range of protein C concentrations was expected to affect clot times more, and a decision whether it was practical to measure protein C with the assay was expected to be possible as a result of assays of the hospital and clinic samples. The results of 56 assayed hospital and clinic samples (already proven to have a normal PT and APTT) and 30 assayed samples from normal control donors are provided below in Table 2.

TABLE 2

Apparent anticoagulant function in clinical samples of plasma selected for normal PT and APTT without prospective regard for the medical history of the patient and in a commercial set of samples of plasma from normal control donors.

|  |  | Patients | Donors |
|---|---|---|---|
| NO APPARENT FUNCTION |  | 20 (36%) | 0 |
| INTERMEDIATE FUNCTION | (+) | 10 (18%) | 1 (3%) |
|  | (++) | 10 (18%) | 3 (10%) |
|  | (+++) | 2 (4%) | 3 (10%) |
| NORMAL FUNCTION |  | 14 (25%) | 23 (77%) |
|  | TOTAL | 56 | 30 |

Far from having all the results show protein C activity, twenty hospital and clinic samples showed no activity. Examining the medical records of those twenty, ten came from patients with a malignancy and two of the ten malignancies had not yet been diagnosed at the time the blood was drawn. Malignancy is often characterized by thrombotic risk. Based on these results, the present invention provides an assay which could serve as an early detection which sensitizes the physician to a potential diagnosis of cancer by revealing an increased risk of thrombosis.

The remaining ten donors were being seen for a thrombotic event or were in an obvious clinical category for thrombotic risk, namely, cardiovascular disease, cerebrovascular disease, congestive heart failure, aneurysm, hypertension, diabetes, etc. Hospital and clinic samples with normal clot times came from individuals who did not have this kind of medical history. Samples with clot times between no activity and normal values came from patients with progressively less clinical evidence of thrombotic risk. Thirty samples of plasma from healthy donors showed apparent anticoagulant activity, though there was one sample with a very low value. Summary statements about the medical condition of patients who provided hospital and clinic plasma are attached hereto in Attachment 1.

Significantly, there was no basis for expecting even one specimen of plasma to show no apparent activity in the assay. Instead, more than one-third of the hospital and clinic samples had clot times of ninety seconds or less, indicating no activity in the protein C system. Based on the foregoing, this inventor must conclude that the protein C system apparently further includes a previously unrecognized soluble, functional component of the protein C system. Such a new soluble component is, and thus the assay of the present invention may be used as, a broadly applicable indicator of thrombotic risk and is useful to sensitize a physician to a potential diagnosis of cancer. In other words, examining the protein C system as a whole permits the assay of the present invention to be used as a broad indicator of thrombotic risk, both primary (hereditary or familial) and secondary (acquired).

With respect to the healthy donors, the assay of the present invention revealed a very large range of clot times. The normal range of values for the assay was expected to be smaller, similar to that of other coagulometric assays. As a result, the large range of normal clot times makes it difficult to use the assay to measure protein C or protein S by plasma dilution techniques. The variation in clot time of individual samples of healthy donor plasma is shown in the table in FIG. 5. The assay used for the column, 0 TM is the APTT. The amount of thrombomodulin added in the assay was reduced from 6 to 5 to 4 µl in an attempt to obtain a clot time under 250 seconds for each sample. In two instances, 3 and 30, the clot time remained above 250 seconds. A pool of normal plasma must be comprised of plasma from many healthy, individual donors, in the face of this kind of variation, to produce a reproducible standard or reference sample. Accordingly, no one, or any mix, of the known variables of the protein C system accounts for these results. The distance in clot time from 90 seconds, where thrombosis and thrombotic risk are predictably seen, to greater than 250 seconds even with a reduction of added thrombomodulin with plasma from ostensibly normal, healthy individuals is indeed remarkable.

PHASE III USE OF HEPARIN ADSORBENT

In order to isolate the variable responsible for the unexpected results and correlations described above, further investigation was initiated. Clearly, the variable is not protein C, protein S, or any of the other known components of the protein C system which have been studied extensively by others. The causative agent has been isolated in an attempt to remove heparin prior to a coagulometric assay, as the assay cannot be used on plasma containing heparin.

Accordingly, in a manner well-known in the art, plasma is treated with a heparin adsorbent. Clinical laboratories have a reagent available to remove heparin prior to a coagulometric assay. This procedure does not change the concentration of coagulation proteins or the underlying PT or APTT. Unexpectedly, plasma without heparin, after treatment with heparin adsorbent, gave no evidence of anticoagulant function in the TM-APTT assay. The APTT was unchanged, but the TM-APTT was reduced to about ninety seconds, the same value seen with protein C- or protein S-deficient plasma. Since the adsorbent does not remove protein C, protein S, or other known components of the protein C system, this result further establishes a previously unrecognized soluble component in the protein C system.

The effect of heparin adsorbent on the TM-APTT of normal plasma is shown in the table of FIG. 5. As seen from the information in FIG. 5, the data is inconsistent with the properties of known components and variables of the protein C system as measured by the TM-APTT. The observed effect of the heparin adsorbent is the removal of a previously unrecognized soluble component of the protein C system.

According to the package insert for heparin adsorbent, "heparin adsorbent is intended for in vitro removal of heparin from patient plasmas without interfering with clotting tests . . . . Sigma Diagnostics Heparin Adsorbent is positively charged ECTEOLA Cellulose resin designed for the in vitro removal of heparin from plasma samples." The basis of effectiveness of the adsorbent is ionic interaction. Since protein C and protein S are in the vitamin K-dependent category of proteins with similar isoelectric point characteristics, one can assume that protein C and protein S are not significantly removed by treatment of plasma with heparin adsorbent. Accordingly, the currently uncharacterized substance appears to have the characteristics that it is soluble, negatively charged, and required for the activation of protein C.

To monitor the presence or absence of this unknown soluble anticoagulant component, which is neither protein C nor protein S, from the protein C system, the following method may be utilized: combining an adsorbent with a first portion of a blood plasma sample; removing said adsorbent from said first portion of said blood plasma sample; then combining said first portion of said blood plasma test sample and a coagulation-activating substance in a calcium-free solution; adding soluble thrombomodulin and calcium ions to the resultant mixture to initiate a coagulation reaction; measuring the time required for said test plasma sample to clot; comparing the measured clot time to that of a second portion of said blood plasma sample; and then using the compared clot time values to monitor the presence or absence of said soluble anticoagulant component.

In addition to detection of the presence or absence of the soluble anticoagulant component, the TM-APTT assay of the present invention may also be utilized to monitor the isolation of the soluble anticoagulant component, which is neither protein C nor protein S, from the protein C system. One method of doing so is to: combining an adsorbent with a blood plasma sample; removing said adsorbent from said blood plasma sample; then combining any solution suspected of containing said soluble anticoagulant component and a coagulation-activating substance in a calcium-free solution; adding soluble thrombomodulin and calcium ions to the resultant mixture to initiate a coagulation reaction; measuring the time required for said sample to clot; comparing the measured clot time to that of a protein C-deficient and a normal control blood plasma sample; and then using the compared clot time values to monitor the presence or absence of a soluble anticoagulant component.

Three groups of patient plasma, in addition to the above-described hospital and clinic group, were examined. The samples came from patients who had a bone marrow transplant or a liver transplant, and from patients treated with Coumadin. Based on the observations in these groups, activity of the protein C system is reduced or absent as a result of myelosuppression and immunosuppression. The assay of the present invention could not be usefully employed on plasma from patients treated with Coumadin, with one exception of a sample of plasma from a patient treated with Coumadin after surgery for removal of malignant bone. Despite prolongation of the PT due to Coumadin therapy, the TM-APTT on this sample, was about ninety seconds, indicative of absent activity of the protein C system.

The present invention thus detects defects in the protein C system including defects in factor VIII and factor V. Defective factor V (mutated factor V, as in the Leiden thrombophilia study well-known in the art) may be determined. However, it should be carefully noted that the present invention is broader in scope than simple detection of defective factor V. As discussed in the background section, the prior art (Sharp, Hajjar, Ridker, et al., etc.) estimates that factor V Leiden which is familial in nature is present in about 5 percent of the general population. For example, Ridker, et al., 1995, found no association between factor V Leiden and myocardial infarction or stroke. However, they found that men with defective factor V had an increased risk for primary venous thrombosis, and it was most apparent among older men. Accordingly, the assays of the prior art have all been directed toward specific components of the protein C system, but have failed to take a holistic approach. The assay of the present invention does not focus on any specific portion (such as the factor V portion) of the protein C system, but rather is directed toward an evaluation of the protein C system as a whole. Accordingly, the assay of the present invention does not encompass a small portion of thrombotic risk, as in the primary (hereditary or familial) venous thrombosis focus of the prior art, but is conservatively expected to encompass well over 75 percent of the thrombosis problem, including primary and secondary venous thrombotic risk, and perhaps up to 90 percent of the thrombosis problem.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, the term "thrombotic risk" is not limited to areas involving arterial and venous subject matter, but also extends to thrombotic syndromes such as thrombophilia (analogous to hemophilia) either inherited or acquired. Clinical conditions associated with acquired thrombophilia may include malignancy, trauma, the post-surgical period, vasculitides, diabetes, stasis from vascular disorders, pregnancy and the use of oral contraceptives.

Thus, the breadth and scope of the present invention should not be limited by any of the above-described exemplary embodiments, but should be defined only in accordance with the following claims appended hereto and their equivalents.

ATTACHMENT 1

SUMMARY STATEMENTS ABOUT THE MEDICAL CONDITION OF PATIENTS WHO PROVIDED HOSPITAL AND CLINIC PLASMA

NO APPARENT ANTICOAGULANT ACTIVITY IN THE TM-APTT ASSAY (CLOT TIME 90 SECONDS OR LESS)

1. Hypertension, aneurysm, arteritis.
2. Breast cancer metastatic to bone.
3. Shortness of breath and throat pain, arrhythmia, atherosclerotic heart disease with a previous infarct, pericarditis, and embolism to the lower extremity, diabetes, old prostate cancer in complete remission.
4. Angina, hypertension, heart valve dysfunction, hypercholesterolemia, lipemia, obesity, segmented glomerulosclerosis.
5. Recurrent stroke, hypertension, hypertensive vascular disease, possible alcohol abuse with some liver dysfunction and cortical atrophy.
6. A newly diagnosed mediastinal adenocarcinoma with involvement of the left main bronchus and the carina.
7. Recurrent squamous cell carcinoma.
8. Recurrent squamous cell carcinoma, hypertension, diabetes.
9. Angina, history of coronary artery disease with recent 4-vessel by-pass surgery, hypertension, history of chronic obstructive pulmonary disease.
10. Terminal rhabdomyosarcoma.
11. Deep vein thrombosis, diabetes, hypertension, atherosclerotic vascular disease, peripheral vascular disease, history of congestive heart failure and chronic obstructive pulmonary disease.
12. Relapsed acute myelogenous leukemia.
13. Newly diagnosed urothelial cell carcinoma.
14. Probable deep vein thrombosis, diabetes, hypertension, peripheral vascular disease, diverticular disease, right paratracheal mass not worked up.

15. Angina, coronary artery disease, previous infarct, hypertension, diabetes.
16. Newly diagnosed vaginal adenocarcinoma, history of Paget's disease of the vulva, chronic lymphocytic leukemia.
17. Extensive Stage I B adenosquamous carcinoma of the cervix with extension to the endometrial cavity, history of diabetes, hypertension, and hypercholesterolemia.
18. Multiple myeloma.
19. Silent myocardial infarct, coronary artery disease, two previous infarcts, cardiac dysrhythmia, congestive heart failure.
20. Acute stroke, hypertension.

INTERMEDIATE ANTICOAGULANT ACTIVITY (+) (CLOT TIME 90–110 SECONDS)

21. Elements of right and left side failure with peripheral edema and with orthopnea and nocturnal dyspnea, no coronary artery disease.
22. Metastatic cervical adenosquamous carcinoma.
23. Newly diagnosed squamous cell carcinoma.
24. Hypertension, history of rheumatic fever.
25. Angina, congestive heart failure, obstructive pulmonary disease, coronary atherosclerosis, history of chronic obstructive pulmonary disease, congestive heart failure, hypertension and previous lower extremity deep vein thrombosis. Patient also has a history of past cervical carcinoma and carries a current pathology report of a low grade squamous epithelial lesion not worked up.
26. Multi-cerebral infarct dementia, diabetes.
27. Hereditary hemorrhagic telangiectasia of the nasal mucosa, tuberous sclerosis.
28. Trauma case (automobile accident), history of hypertension.
29. Recurrent and metastatic fibrolamellar hepatoma.
30. Self-resolving jaundice and liver disease of unknown etiology.

INTERMEDIATE ANTICOAGULANT ACTIVITY (++) CLOT TIME 110–130 SECONDS)

31. Nausea with epigastric pain, diffuse gastritis and erosive duodenitis, some irregularity in vital signs.
32. History of Hodgkin's disease with possible recurrence.
33. Hypercholesterolemia with morbid obesity.
34. Tylenol overdose.
35. Newly diagnosed metastatic carcinoma with renal primary.
36. Common variable hypogammaglobulinemia (congenital).
37. Eighty-eight year old died of cardiac arrest secondary to arrhythmia, recent history of chronic arrhythmia with pacemaker placement.
38. Deep vein thrombosis in the lower extremity, previous history of deep vein thrombosis, morbid obesity.
39. History of osteoarthritis, degenerative hip and shoulder disease, diverticulitis, irritable colon and severe bowel management problems.
40. Diabetes well controlled, recent recipient of vigorous diabetes management program as a result of developing hypertension, increasing neuropathy and peripheral vascular insufficiency.

INTERMEDIATE ANTICOAGULANT ACTIVITY (+++) (CLOT TIME 130–150 SECONDS)

41. Chronic otitis media and eustachian tube dysfunction.
42. Non-viable incomplete abortion.

NORMAL ANTICOAGULANT ACTIVITY (CLOT TIME 150 SECONDS OR GREATER)

43. Chronic sinusitis, history of asthma.
44. Alcohol abuse with some liver dysfunction and cortical atrophy.
45. Chronic ear disease since childhood with hearing loss, overweight, history of peptic ulcer.
46. Osteoarthrosis, hospitalized for hip replacement, history of Meniere's disease with decreased hearing, exercise-induced asthma, increased thyroid function (not medicated), previous medical history of hypertension and an abnormal EKG (no mention of medication or current status).
47. History of chronic ear disease.
48. Nasal polyposis, pansinusitis, and allergic rhinitis.
49. Revision rhinoplasty.
50. Recurrent (parotid?) adenocarcinoma 14 days post-chemotherapy.
51. Septoplasty for deviated nasal septum.
52. Chronic lower back pain with multiple back surgeries.
53. Early diagnosis of Stage I B squamous cell carcinoma of the cervix in an otherwise healthy woman.
54. Eighty-three year old with a previous medical history of chronic obstructive pulmonary disease, hypertension, and a porcine valve replacement for aortic stenosis four years earlier and a mild stroke in 1979, now completely asymptomatic. Patient also has an old prostate carcinoma in complete remission.
55. Previous diagnosis of liver dysfunction of unknown etiology, obesity, past history of adult onset diabetes without hypercholesterolemia or any complaints of vascular disease.
56. Reflux laryngitis, chronic gastric reflux.

What is claimed is:

1. A one-stage blood coagulation assay for determining risk of thrombosis of an individual by examining the protein C system in a blood plasma test sample, said method comprising:
   a) combining a blood plasma test sample and a coagulation-activating substance in a calcium-free solution;
   b) adding soluble thrombomodulin and calcium ions to the resultant mixture to initiate a coagulation reaction;
   c) measuring the time required for said blood plasma sample to clot;
   d) comparing the measured clot time to that of standard control plasma samples; and
   e) using the compared clot time values for determining whether the individual from whom said blood plasma sample was taken has a risk of thrombosis.

2. The assay of claim 1 wherein said blood plasma test sample is obtained from a human donor.

3. The assay of claim 2 wherein said human donor is a clinical subject.

4. The assay of claim 1 wherein said coagulation-activating substance is a negatively charged organic molecule.

5. The assay of claim 4 wherein said negatively charged molecule is ellagic acid.

6. The assay of claim 1 wherein said standard control plasma samples are normal control plasma samples, derived from one or more normal healthy donors, and which contain statistically-common and expected amounts of all known coagulation-related factors.

7. The assay of claim 1 wherein said assay further comprises combining said blood plasma test sample, said coagulation-activating substance, and a micellar surface in said calcium-free solution.

8. The assay of claim 7, wherein said micellar surface is provided by a cephalin derived from rabbit brain tissue.

9. A one-stage blood coagulation assay for monitoring the isolation of a soluble anticoagulant component, which is neither protein C nor protein S, from the protein C system, said method comprising:
   a) combining an adsorbent with a blood plasma sample;
   b) removing said adsorbent from said blood plasma sample;
   c) after removing said adsorbent, combining said blood plasma sample with any solution suspected of containing said soluble anticoagulant component and a coagulation-activating substance in a calcium-free solution;
   d) adding soluble thrombomodulin and calcium ions to the resultant mixture to initiate a coagulation reaction;
   e) measuring the time required for said sample to clot;
   f) comparing the measured clot time to that of a protein C-deficient and a normal control blood plasma sample; and
   g) using the compared clot time values to monitor the presence or absence of said soluble anticoagulant component.

10. The assay of claim 9, wherein said adsorbent is a positively charged ion-exchange resin.

11. The assay of claim 9, wherein said adsorbent is a cellulose resin.

12. The assay of claim 9, wherein said adsorbent is a heparin adsorbent.

13. A one-stage blood coagulation assay for sensitizing a physician to a potential diagnosis of cancer in an individual by examining the protein C system, said method comprising:
   a) combining a blood plasma test sample and a coagulation-activating substance in a calcium-free solution;
   b) adding soluble thrombomodulin and calcium ions to the resultant mixture to initiate a coagulation reaction;
   c) measuring the time required for said plasma sample to clot;
   d) comparing the measured clot time to that of standard control plasma samples; and
   e) using the compared clot time values for determining whether the individual from whom said plasma sample was taken has an increased risk of thrombosis and potentially diagnosing the presence of an occult cancer.

* * * * *

UNITED STATES PATENT AND TRADEMARK OFFICE
CERTIFICATE OF CORRECTION

PATENT NO. : 5,716,795
DATED : Feb. 10, 1998
INVENTOR(S) : John T. Matschiner

It is certified that error appears in the above-identified patent and that said Letters Patent is hereby corrected as shown below:

Column 6, line 4:
    delete "thrombomodutin: and therefore insert --thrombomodulin --

Column 14, line 18:
    insert before Deficient --*--

Signed and Sealed this

Twenty-first Day of April, 1998

Attest:

BRUCE LEHMAN

Attesting Officer     Commissioner of Patents and Trademarks